United States Patent [19]

Ogawa et al.

[11] Patent Number: 5,462,925

[45] Date of Patent: Oct. 31, 1995

[54] TRANSFORMING GROWTH FACTOR β2,3

[75] Inventors: Yasushi Ogawa, Pacifica; David Schmidt, Santa Cruz; James Dasch, Palo Alto, all of Calif.

[73] Assignee: Celtrix Pharmaceuticals, Inc., Santa Clara, Calif.

[21] Appl. No.: 979,441

[22] Filed: Nov. 20, 1992

Related U.S. Application Data

[63] Continuation of Ser. No. 614,306, Nov. 16, 1990, abandoned.

[51] Int. Cl.$^6$ .................. A61K 37/24; A61K 37/36
[52] U.S. Cl. ............... 514/12; 530/324; 530/350; 530/399; 930/10; 930/120
[58] Field of Search ............... 530/399, 324, 530/350; 514/12

[56] References Cited

U.S. PATENT DOCUMENTS

| 4,806,523 | 2/1989 | Bentz et al. | 514/2 |
|---|---|---|---|
| 4,843,063 | 6/1989 | Seyedin et al. | 514/2 |
| 4,886,747 | 12/1989 | Derynck et al. | 435/240.2 |
| 4,931,548 | 6/1990 | Lucas | 514/886 |

FOREIGN PATENT DOCUMENTS

| WO8401106 | 3/1984 | WIPO. |
|---|---|---|
| WO8805788 | 7/1988 | WIPO. |
| WO9000900 | 2/1990 | WIPO. |

OTHER PUBLICATIONS

R. de Martin et al., *EMBO J.* 6:3673–3677 (1987).
*Peptides, Synthesis–Structure–Function;* ed. by Rich et al., Pierce Chemical Co. Rockford, Ill. 1981, p. 529.
*Methods for Preparation of Media, Supplements, and Substrata for Serum–Free Animal Cell Culture* (1984) Alan R. Liss, Inc., New York, Chapter 9, pp. 181–194.
Cheifetz et al., *Cell*(1987) 48:409–415.
Graycar et al., *Mol. Endocrinol.* (1989) 3(12):1977–1985.
Derynck et al., *EMBO J.* (1988) 7(12):3737–3743.
Lefer et al., *Science* (1990) 249:61–64.
Chen et al., *J. Bone & Mineral Res.* (1990) 5:580 (abstract No. 26).
Dijke et al., *Proc. Natl. Acad. Sci.* (1988) 85:4715–4719.
Roberts et al., *Growth Factors* (1990) 2:135–147.
Jakowlew et al., *Mol. Endocrinol.* (1988) 2(8):747–755.
Jakowlew et al., *Mol. Endocrinol.* (1988) 2(12):1186–1195.

*Primary Examiner*—F. T. Moezie
*Attorney, Agent, or Firm*—Morrison & Foerster

[57] ABSTRACT

A heterodimeric form of TGF-β is described. This 25 KD molecule is active in an in vitro assay of inhibition of epithelial cell growth. The protein may be isolated from bone. When reduced, the protein elutes in two peaks by RP-HPLC. In immunoblots, the reduced protein from the earlier eluting peak reacts predominately with antibodies directed against TGF-β3, while reduced protein from the later eluting peak reacts predominately with antibodies directed against TGF-β2. The N-terminal amino acid sequence and immunoreactivity of the native protein are consistent with a heterodimer of TGF-β2 and TGF-β3.

2 Claims, 7 Drawing Sheets

Bovine TGF-β2.3 N-Terminal Sequence

Ala-Leu-Asp-Ala-Ala-Tyr-Xxx$^1$-Phe-Arg-Asn
          Thr  Asn

Val-Gln-Asp-Asn-Xxx$^1$-Xxx$^1$-Leu-Arg-Pro-Leu
Leu Glu Glu              Val

Tyr-Ile-Asp-Phe-Lys-Arg-Asp-Leu-Gly-Xxx$^2$
          Arg Gln

Lys-Trp-Ile-His-Glu-Pro-Lys-Gly-Tyr-Asn
    Val                      Tyr

Ala-Asn-Phe-Xxx$^1$-Ala-Gly-Ala-Xxx$^1$-Xxx$^3$-Tyr
         Ser     Pro          Pro

Leu-Trp-Ser-Ser-Asp-Thr-Xxx$^5$-Xxx$^6$-Xxx$^7$
Tyr Xxx$^4$Arg Tyr     Ala
        Leu            Gly
        Thr           Ile
                    Leu
                    Pro
                    Tyr
                    Val

Xxx$^1$=Cys            Xxx$^4$=Arg           Xxx$^7$=Ser

Xxx$^2$=Trp            Xxx$^5$=Gln/Thr

Xxx$^3$=Pro            Xxx$^6$=His

Figure 6A

1. HUMAN TGF-β1
2. HUMAN TGF-β2
3. HUMAN TGF-β3

```
1                 5                      10                      15
ALA-LEU-ASP-THR-ASN-TYR-CYS-PHE-SER-SER-THR-GLU-LYS-ASN-CYS-
ALA-LEU-ASP-ALA-ALA-TYR-CYS-PHE-ARG-ASN-VAL-GLN-ASP-ASN-CYS-
ALA-LEU-ASP-THR-ASN-TYR-CYS-PHE-ARG-ASN-LEU-GLU-GLU-ASN-CYS- 16                20                     25                      30
CYS-VAL-ARG-GLN-LEU-TYR-ILE-ASP-PHE-ARG-LYS-ASP-LEU-GLY-TRP-
CYS-LEU-ARG-PRO-LEU-TYR-ILE-ASP-PHE-LYS-ARG-ASP-LEU-GLY-TRP-
CYS-VAL-ARG-PRO-LEU-TYR-ILE-ASP-PHE-ARG-GLN-ASP-LEU-GLY-TRP- 31                35                     40                      45
LYS-TRP-ILE-HIS-GLU-PRO-LYS-GLY-TYR-HIS-ALA-ASN-PHE-CYS-LEU-
LYS-TRP-ILE-HIS-GLU-PRO-LYS-GLY-TYR-ASN-ALA-ASN-PHE-CYS-ALA-
LYS-TRP-VAL-HIS-GLU-PRO-LYS-GLY-TYR-TYR-ALA-ASN-PHE-CYS-SER- 46                50                     55                      60
GLY-PRO-CYS-PRO-TYR-ILE-TRP-SER-LEU-ASP-THR-GLN-TYR-SER-LYS-
GLY-ALA-CYS-PRO-TYR-LEU-TRP-SER-SER-ASP-THR-GLN-HIS-SER-ARG-
GLY-PRO-CYS-PRO-TYR-LEU-ARG-SER-ALA-ASP-THR-THR-HIS-SER-THR- 61                65                     70                      75
VAL-LEU-ALA-LEU-TYR-ASN-GLN-HIS-ASN-PRO-GLY-ALA-SER-ALA-ALA-
VAL-LEU-SER-LEU-TYR-ASN-THR-ILE-ASN-PRO-GLU-ALA-SER-ALA-SER-
VAL-LEU-GLY-LEU-TYR-ASN-THR-LEU-ASN-PRO-GLU-ALA-SER-ALA-SER- 76                80                     85                      90
PRO-CYS-CYS-VAL-PRO-GLN-ALA-LEU-GLU-PRO-LEU-PRO-ILE-VAL-TYR-
PRO-CYS-CYS-VAL-SER-GLN-ASP-LEU-GLU-PRO-LEU-THR-ILE-LEU-TYR-
PRO-CYS-CYS-VAL-PRO-GLN-ASP-LEU-GLU-PRO-LEU-THR-ILE-LEU-TYR- 91                95                     100                     105
TYR-VAL-GLY-ARG-LYS-PRO-LYS-VAL-GLU-GLN-LEU-SER-ASN-MET-ILE-
TYR-ILE-GLY-LYS-THR-PRO-LYS-ILE-GLU-GLN-LEU-SER-ASN-MET-ILE-
TYR-VAL-GLY-ARG-THR-PRO-LYS-VAL-GLU-GLN-LEU-SER-ASN-MET-VAL- 106            110
VAL-ARG-SER-CYS-LYS-CYS-SER
VAL-LYS-SER-CYS-LYS-CYS-SER
VAL-LYS-SER-CYS-LYS-CYS-SER
```

1. TGF-β1: R. DERYNCK ET AL., J. BIOL. CHEM. (1986) 261, 4377-4379.
2. TGF-β2: H. MARQUARDT ET AL., J. BIOL. CHEM. (1987) 262, 12127-12131.
3. TGF-β3: P. TEN DIJKE ET AL., PROC. NATL. ACAD. SCI. USA (1988) 85, 4715-4719.

Figure 6B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ala  Leu  Asp  Thr  Asn  Tyr  Cys  Phe  Ser  Ser  Thr  Glu  Lys  Asn  Cys  Cys
 1                   5                        10                       15

Val  Arg  Gln  Leu  Tyr  Ile  Asp  Phe  Arg  Lys  Asp  Leu  Gly  Trp  Lys  Trp
               20                       25                       30

Ile  His  Glu  Pro  Lys  Gly  Tyr  His  Ala  Asn  Phe  Cys  Leu  Gly  Pro  Cys
          35                        40                       45

Pro  Tyr  Ile  Trp  Ser  Leu  Asp  Thr  Gln  Tyr  Ser  Lys  Val  Leu  Ala  Leu
     50                        55                       60

Tyr  Asn  Gln  His  Asn  Pro  Gly  Ala  Ser  Ala  Ala  Pro  Cys  Cys  Val  Pro
65                        70                       75                       80

Gln  Ala  Leu  Glu  Pro  Leu  Pro  Ile  Val  Tyr  Tyr  Val  Gly  Arg  Lys  Pro
               85                            90                       95

Lys  Val  Glu  Gln  Leu  Ser  Asn  Met  Ile  Val  Arg  Ser  Cys  Lys  Cys  Ser
               100                      105                      110
```

( 2 ) INFORMATION FOR SEQ ID NO:2:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ala  Leu  Asp  Ala  Ala  Tyr  Cys  Phe  Arg  Asn  Val  Gln  Asp  Asn  Cys  Cys
 1                   5                        10                       15

Leu  Arg  Pro  Leu  Tyr  Ile  Asp  Phe  Lys  Arg  Asp  Leu  Gly  Trp  Lys  Trp
               20                       25                       30

Ile  His  Glu  Pro  Lys  Gly  Tyr  Asn  Ala  Asn  Phe  Cys  Ala  Gly  Ala  Cys
          35                        40                       45

Pro  Tyr  Leu  Trp  Ser  Ser  Asp  Thr  Gln  His  Ser  Arg  Val  Leu  Ser  Leu
     50                        55                       60

Tyr  Asn  Thr  Ile  Asn  Pro  Glu  Ala  Ser  Ala  Ser  Pro  Cys  Cys  Val  Ser
65                        70                       75                       80
```

```
Gln  Asp  Leu  Glu  Pro  Leu  Thr  Ile  Leu  Tyr  Tyr  Ile  Gly  Lys  Thr  Pro
               85                       90                      95

Lys  Ile  Glu  Gln  Leu  Ser  Asn  Met  Ile  Val  Lys  Ser  Cys  Lys  Cys  Ser
               100                      105                     110
```

(2) INFORMATION FOR SEQ ID NO:3:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:3:

```
Ala  Leu  Asp  Thr  Asn  Tyr  Cys  Phe  Arg  Asn  Leu  Glu  Glu  Asn  Cys  Cys
1                   5                       10                      15

Val  Arg  Pro  Leu  Tyr  Ile  Asp  Phe  Arg  Gln  Asp  Leu  Gly  Trp  Lys  Trp
               20                       25                      30

Val  His  Glu  Pro  Lys  Gly  Tyr  Tyr  Ala  Asn  Phe  Cys  Ser  Gly  Pro  Cys
          35                       40                      45

Pro  Tyr  Leu  Arg  Ser  Ala  Asp  Thr  Thr  His  Ser  Thr  Val  Leu  Gly  Leu
     50                       55                      60

Tyr  Asn  Thr  Leu  Asn  Pro  Glu  Ala  Ser  Ala  Ser  Pro  Cys  Cys  Val  Pro
65                       70                      75                      80

Gln  Asp  Leu  Glu  Pro  Leu  Thr  Ile  Leu  Tyr  Tyr  Val  Gly  Arg  Thr  Pro
               85                       90                      95

Lys  Val  Glu  Gln  Leu  Ser  Asn  Met  Val  Val  Lys  Ser  Cys  Lys  Cys  Ser
               100                      105                     110
```

(2) INFORMATION FOR SEQ ID NO:4:

(i) SEQUENCE CHARACTERISTICS:
        (A) LENGTH: 59 amino acids
        (B) TYPE: amino acid
        (D) TOPOLOGY: linear (ii) MOLECULE TYPE: protein (ix) FEATURE:
        (A) NAME/KEY: Modified-site
        (B) LOCATION: 4
        (D) OTHER INFORMATION: /note="This position is Ala or Thr."

(ix) FEATURE:
        (A) NAME/KEY: Modified-site
        (B) LOCATION: 5
        (D) OTHER INFORMATION: /note="This position is Ala or Asn."

(ix) FEATURE:
        (A) NAME/KEY: Modified-site
        (B) LOCATION: 11
        (D) OTHER INFORMATION: /note="This position is Val or Leu."

(ix) FEATURE:
        (A) NAME/KEY: Modified-site
        (B) LOCATION: 12
        (D) OTHER INFORMATION: /note="This position is Gln or Glu."

(ix) FEATURE:
        (A) NAME/KEY: Modified-site
        (B) LOCATION: 13
        (D) OTHER INFORMATION: /note="This site is Asp or Glu."

( i x ) FEATURE:
   ( A ) NAME/KEY: Modified-site
   ( B ) LOCATION: 17
   ( D ) OTHER INFORMATION: /note="This position is Leu or
     Val."

( i x ) FEATURE:
   ( A ) NAME/KEY: Modified-site
   ( B ) LOCATION: 25
   ( D ) OTHER INFORMATION: /note="This position is Lys or
     Arg."

( i x ) FEATURE:
   ( A ) NAME/KEY: Modified-site
   ( B ) LOCATION: 26
   ( D ) OTHER INFORMATION: /note="This position is Arg or
     Gln."

( i x ) FEATURE:
   ( A ) NAME/KEY: Modified-site
   ( B ) LOCATION: 33
   ( D ) OTHER INFORMATION: /note="This position is Ile or
     Val."

( i x ) FEATURE:
   ( A ) NAME/KEY: Modified-site
   ( B ) LOCATION: 40
   ( D ) OTHER INFORMATION: /note="This position is Asn or
     Tyr."

( i x ) FEATURE:
   ( A ) NAME/KEY: Modified-site
   ( B ) LOCATION: 45
   ( D ) OTHER INFORMATION: /note="This position is Ala or
     Ser."

( i x ) FEATURE:
   ( A ) NAME/KEY: Modified-site
   ( B ) LOCATION: 47
   ( D ) OTHER INFORMATION: /note="This position is Ala or
     Pro."

( i x ) FEATURE:
   ( A ) NAME/KEY: Modified-site
   ( B ) LOCATION: 50
   ( D ) OTHER INFORMATION: /note="This position is Tyr or
     Pro."

( i x ) FEATURE:
   ( A ) NAME/KEY: Modified-site
   ( B ) LOCATION: 51
   ( D ) OTHER INFORMATION: /note="This position is Leu or
     Tyr."

( i x ) FEATURE:
   ( A ) NAME/KEY: Modified-site
   ( B ) LOCATION: 52
   ( D ) OTHER INFORMATION: /note="This position is Trp or
     Arg."

( i x ) FEATURE:
   ( A ) NAME/KEY: Modified-site
   ( B ) LOCATION: 53
   ( D ) OTHER INFORMATION: /note="This position is Ser, Arg,
     Leu, or Thr."

( i x ) FEATURE:
   ( A ) NAME/KEY: Modified-site
   ( B ) LOCATION: 54
   ( D ) OTHER INFORMATION: /note="This position is Ser or
     Tyr."

( i x ) FEATURE:
   ( A ) NAME/KEY: Modified-site
   ( B ) LOCATION: 56
   ( D ) OTHER INFORMATION: /note="This position is Thr, Ala,
     Gly, Ile, Leu, Pro, Tyr, or Val."

( i x ) FEATURE:

( A ) NAME/KEY: Modified-site
( B ) LOCATION: 57
( D ) OTHER INFORMATION: /note="This position is Gln or Thr."

( x i ) SEQUENCE DESCRIPTION: SEQ ID NO:4:

```
Ala Leu Asp Xaa Xaa Tyr Cys Phe Arg Asn Xaa Glx Xaa Asn Cys Cys
 1               5                      10                  15

Xaa Arg Pro Leu Tyr Ile Asp Phe Xaa Xaa Asp Leu Gly Trp Lys Trp
            20                  25                  30

Xaa His Glu Pro Lys Gly Tyr Xaa Ala Asn Phe Cys Xaa Gly Xaa Cys
        35                  40                  45

Pro Xaa Xaa Xaa Xaa Xaa Asp Xaa Xaa His Ser
    50                  55
```

TRANSFORMING GROWTH FACTOR β2,3

This application is a continuation, of application Ser. No. 07/614,306, filed Nov. 16, 1990, now abandoned.

TECHNICAL FIELD

The present invention relates to protein chemistry. More particularly, it relates to the discovery and isolation of a new form of transforming growth factor β.

BACKGROUND

PCT WO 84/001106, filed 23 Sep. 1983, describes transforming growth factor β1 (TGF-β1) and its use for the promotion of cell proliferation and tissue repair, wound healing, and treatment of traumata.

U.S. Pat. No. 4,848,063 describes two cartilage inducing factors, CIF-A and CIF-B, found in mammalian bone that (1) are cofactors for inducing cartilage formation in vivo; (2) promote connective tissue deposition in vivo in the absence of any added activating agent or cofactor, and (3) are active in the anchorage-independent cell growth assay used to characterize TGF-β (this assay is sometimes called the TGF-β assay herein and is described in *Methods for Preparation of Media, Supplements, and Substrate for Serum-free Animal Cell Culture* (1984) pp. 181–194, Alan R. Liss, Inc.).

U.S. Pat. No. 4,806,523, filed 6 Mar. 1986, discloses that CIF-A and CIF-B both possess anti-inflammatory activity and are inhibitors of mitogen stimulated T cell proliferation and B cell activation. It also reports that CIF is localized in centers of hematopoiesis and lymphopoiesis and that CIF may, therefore, be useful for treating indications associated with malfunction or dysfunction of hematopoiesis or lymphopoiesis. CIF-A has since been shown to be identical to TGF-β1. CIF-B has since been recognized as a new form of β-type transforming growth factor and is now called TGF-β2.

U.S. Pat. No. 4,886,747 discloses a third β-type transforming growth factor called TGF-β3.

TGF-β1, TGF-β2, and TGF-β3 are all composed of two identical polypeptide chains linked by disulfide bonds, i.e., they are homodimers. The heterodimer of TGF-β1 and TGF-β2, called TGF-β1.2, has been identified and its uses demonstrated. PCT WO 88/05788, filed 29 Jan. 1988, discloses a heterodimer of TGF-β1 and TGF-β2. PCT WO 90/00900, filed 20 Jul. 1989, discloses treatment of inflammatory disorders with homodimeric TGF-β1 and 2, and the heterodimer TGF-β1.2.

DISCLOSURE OF THE INVENTION

The invention provides a previously unknown form of TGF-β that is found in bone and methods for obtaining the same in substantially pure form from bone or from recombinant expression in vitro. This TGF-β, denoted TGF-β2.3 (whose partial sequence is SEQ ID NO:4), is a heterodimer of TGF-β2 (SEQ ID NO:2) and TGF-β3 (SEQ ID NO:3), and is active in an in vitro assay of inhibition of epithelial cell growth.

Accordingly, one aspect of the invention is substantially pure TGF-β2.3. In another aspect, a chondrogenic/osteogenic effective amount of TGF-β2.3 with a substantially nonimmunogenic carrier is formulated as a chondrogenic/osteogenic implant composition. In a further aspect an effective amount of TGF-β2.3 with a pharmaceutically acceptable carrier is formulated as a composition for promoting proliferation of normal cells.

Another aspect of the invention is a process for preparing TGF-β2.3 from bone, comprising the steps of pooling side fractions from peaks of column chromatography, subjecting those fractions to reverse phase HPLC and recovering those fraction which migrate more slowly than TGF-β2 by SDS-PAGE, subjecting those slower migrating fractions to FPLC and recovering those that migrate during a pH 4.6 to 6.7 gradient, subjecting the pH 4.6 to 6.7 eluant to reverse phase HPLC or gel electrophoresis, and recovering substantially pure TGF-β2.3.

Another aspect of the invention is a method of inducing cartilage and/or bone formation at a predetermined site with an implant of TGF-β2.3.

Another aspect of the invention is a method for treating a patient for osteoporosis with a therapeutically effective amount of a parenteral formulation of TGF-β2.3 administered parenterally.

Another aspect of the invention is a method for treating a patient for inflammation with an anti-inflammatory effective amount of TGF-β2.3. A further aspect of the invention is a method for preventing or reducing local inflammation to a solid implant made of a permeable material by dispersing an anti-inflammatory effective amount of TGF-β2.3 in the material.

An additional aspect of the invention is a method for treating a patient for an indication associated with dysfunction or malfunction of hematopoiesis or lymphopoiesis with an effective amount of TGF-β2.3.

Another aspect of the invention is a method for inhibiting the growth of tumor cells in a mammal by administering to that mammal an oncostatically effective amount of TGF-β2.3.

Another aspect of the invention is a method for producing TGF-β2.3 by joining the DNA sequence encoding the N-terminal signal sequence and proregion of TGF-β2 or TGF-β3 to the DNA sequence encoding the mature sequence of TGF-β3 or TGF-β2 to generate a chimeric construct, introducing the chimeric construct in an expression vector into a host cell, introducing a TGF-β2 or TGF-β3 precursor gene in an expression vector into the host cell, wherein the TGF-β2 or TGF-β3 precursor gene has an N-terminal signal sequence and proregion substantially corresponding to N-terminal signal sequence region in the chimeric construct, and recovering TGF-β2.3 from the host cell.

A further aspect of the invention is a method for preventing severe cardiac injury resulting from reperfusion of ischemic myocardium comprising administering an effective amount of TGF-β2.3 to a patient, prior to or after the onset of ischemia.

Another aspect of the invention is a method for the treatment of septic shock in an animal comprising administering an effective amount of TGF-β2.3 to the animal.

A further aspect of the invention is a method for protecting hematopoietic stem cells in a patient from the myelotoxicity of chemotherapeutic drugs comprising administering an effective amount of TGF-β2.3 to the patient prior to exposure to the chemotherapeutic drugs.

A further aspect of the invention is a method for protecting hematopoietic stem cells in a patient from the myelotoxicity of radiation therapy comprising administering an effective amount of TGF-β2.3 to the patient prior to exposure to the radiation therapy.

A further aspect of the invention is a method for diagnosing a disorder involving the production of TGF-β2, TGF-β3, or TGF-β2.3, using as a diagnostic reagent TGF-β2.3 protein, or monoclonal antibodies or polyclonal antibodies directed against TGF-β2.3.

Another aspect of the invention is a method for treating acute and chronic disease states that result from overproduction of TGF-β2, 3, or 2.3, by administering a therapeutically effective amount of a monoclonal antibody reactive with TGF-β2.3, or an antigen-binding fragment of a monoclonal antibody reactive with TGF-β2.3.

Another aspect of the invention is a method for treating tumor cells that produce TGF-β2, 3, or 2.3, by administering a therapeutically effective amount of a monoclonal antibody reactive with TGF-β2.3 to suppress the immunosuppressive effects of TGF-β.

Another aspect of the invention is a method for treating metastatic cancers by administering a therapeutically effective amount of a monoclonal antibody reactive with TGF-β2.3 to mark tumor cells for destruction by complement or by immune cells dedicated to tumor removal These and other embodiments of the present invention will readily occur to those of ordinary skill in view of the disclosure herein.

BRIEF DESCRIPTION OF THE FIGURES

FIG. 6A shows the N-terminal amino acid sequence of the TGF-β2.3 heterodimer of the instant invention.

FIG. 6B shows the amino acid sequences of TGF-β1, TGF-62 2, and TGF-β3.

DETAILED DESCRIPTION

Figure 1:
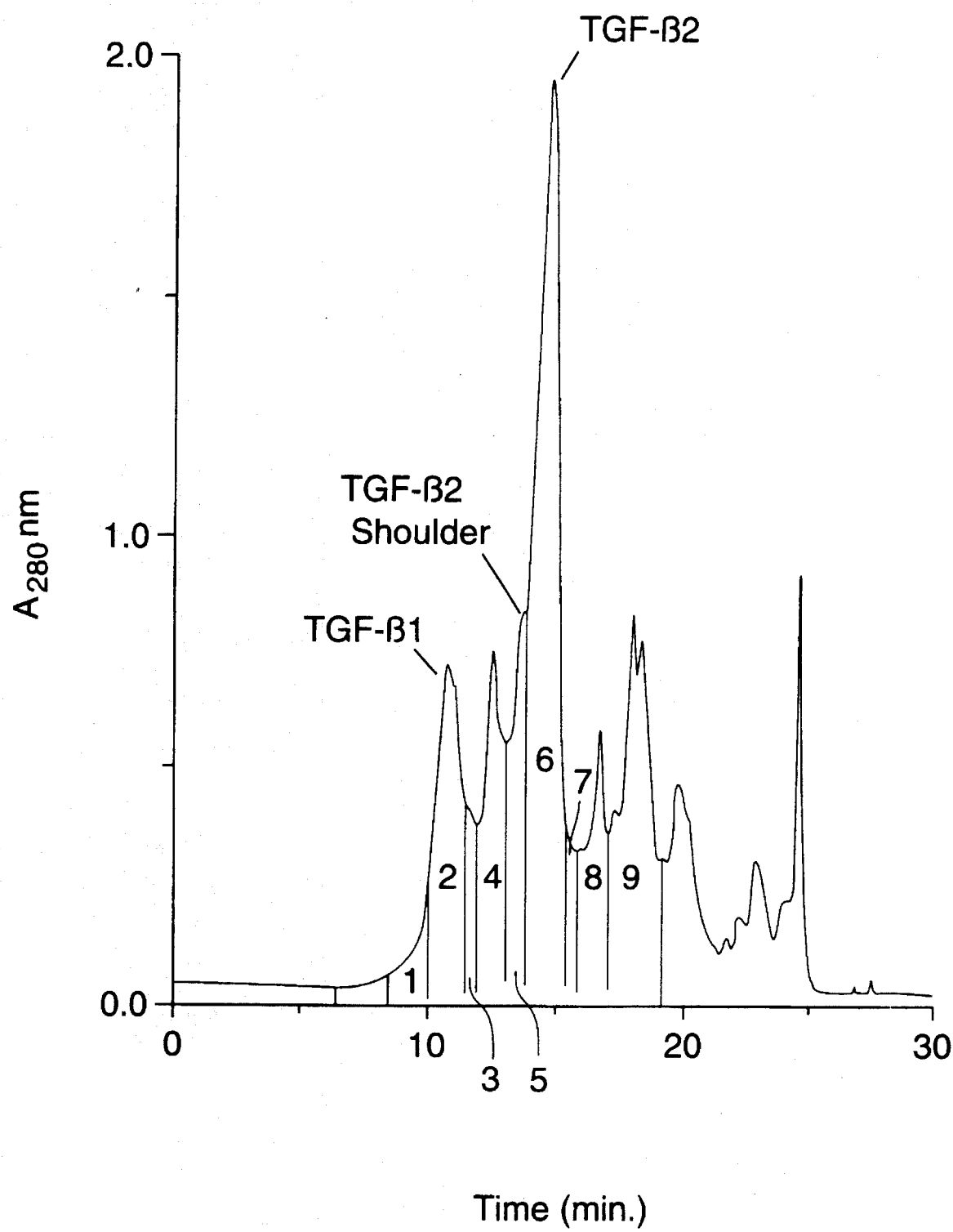
FIG. 1 is the elution profile of TGF-β2 peak fractions prepared by cation exchange chromatography, applied to a C18 RP-HPLC column and eluted with a linear acetonitrile gradient in 0.1% trifluoroacetic acid (TFA).

The practice of the present invention will employ, unless otherwise indicated, conventional techniques of synthetic organic chemistry, protein chemistry, molecular biology, microbiology, and recombinant DNA technology, which are within the skill of the art. Such techniques are explained fully in the literature. See, e.g., Scopes, R. K., *Protein Purification Principles and Practices*, 2d ed. (Springer-Verlag, 1987), *Methods in Enzymology* (S. Colowick and N. Kaplan, est., Academic Press, Inc.), Sambrook et al., *Molecular Cloning: A Laboratory Manual*, 2d ed., Cold Spring Harbor Press, Cold Spring Harbor, NY, 1989, *Handbook of Experimental Immunology*, Vols. I–IV (D. M. Weir and C. C. Blackwell, est., 1986, Blackwell Scientific Publications); House, *Modern Synthetic Reactions*, 2nd ed., Benjamin/Cummings, Menlo Park, Calif., 1972.

All patents, patent applications, and publications mentioned herein, whether supra or infra, are hereby incorporated by reference in their entirety.

A. Definitions

In defining the present invention, the following terms will be employed, and are intended to be defined as indicated below.

As used herein the term "treat" is intended to mean prophylaxis or attenuation of an existing condition. Accordingly, in the case of inflammation, the invention method may be used to prevent inflammation or alleviate existing inflammation.

As used herein the term "inflammation" is intended to encompass both acute responses (i.e. a response in which the inflammatory processes are active) and chronic responses (i.e. a response marked by slow progress and formation of new connective tissue). Chronic and acute inflammation may be distinguished by the cell types involved. Acute inflammation often involves polymorphonuclear neutrophils; whereas chronic inflammation is normally characterized by a lymphohistiocytic and/or granulomatous response. Examples of specific types of inflammation are diffuse inflammation, focal inflammation, croupous inflammation, interstitial inflammation, obliterative inflammation, reactive inflammation, specific inflammation, toxic inflammation, and traumatic inflammation.

As used herein, the term "septic shock" refers to the sequence of events triggered by bacteremia during which cell wall substances (endotoxin in Gram-negative organisms and peptidoglycan/teichoic acid complex in Gram-positive organisms) activate the complement, kinin, and ACTH/endorphin systems. This series of metabolic events ultimately progresses to a state of shock.

As used herein, a protein is substantially pure when that protein has been purified to the extent that it is essentially free of other molecules with which it is associated in nature. In this regard, the term "substantially pure" intends a composition containing less than about 30% by weight contaminating protein, preferably less than about 10% contaminating protein, and most preferably less than about 5% by weight contaminating protein. The term "substantially pure" is used relative to proteins with which the TGF-β2.3 is associated in nature and is not intended to exclude compositions in which the TGF-β2.3 is admixed with nonproteinaceous pharmaceutical carriers or vehicles or proteinaceous pharmaceutical carriers or vehicles.

As used herein, an amino acid sequence substantially corresponding to TGF-β2 will have at least 80% sequence homology with the amino acid sequence of TGF-β2. Similarly, an amino acid sequence substantially corresponding to TGF-β3 will have at least 80% sequence homology with the amino acid sequence of TGF-β3.

As used herein, a DNA sequence substantially corresponding to TGF-β2 will have at least 80% sequence homology with the DNA sequence of TGF-β2. Similarly, a DNA sequence substantially corresponding to TGF-β3 will have at least 80% sequence homology with the DNA sequence of TGF-β3.

As used herein, an "expression vector" refers to a plasmid, bacteriophage, virus, or other molecule into which a gene of interest may be cloned, such that the appropriate signals for expression of that gene are present on that vector. Expression vectors may require regulation of expression by factors provided in trans.

As used herein, the terms "monoclonal antibody" and "Mab" refer to an immunoglobulin composition having a substantially homogeneous population of antibodies, each of which binds to the same antigenic determinant. Unless otherwise indicated, the term is not intended to be limited to antibodies of any particular mammalian species or isotype, or to antibodies prepared in any given manner. The term is intended to include whole antibody molecules as well as antigen-binding fragments (e.g., Fab', F(ab')$_2$).

B. General Methods

The present invention relates to TGF-$\beta$2.3, a novel $\beta$-type transforming growth factor. TGF-$\beta$s isolated to date from natural sources are polypeptide dimers of approximately 25 to 26 KD molecular weight as determined by SDS-PAGE. TGF-$\beta$2.3 is a heterodimer of TGF-$\beta$2 and TGF-$\beta$3.

A procedure for isolating TGF-$\beta$s from bovine bone is described in U.S. Pat. No. 4,843,063, which is incorporated herein by reference in its entirety. It involves extracting demineralized bone (DMB) with an extractant (e.g. $\geq$4M guanidine hydrochloride, 8M urea) that solubilizes nonfibrous proteins, gel filtering the extract to obtain a <30 KD fraction on carboxymethylcellulose (CMC) at pH 4.5–5.5, preferably 4.8, eluting the CMC-absorbed fraction with an NaCl gradient, and purifying the proteins from the portion eluting at about 150–250 mM NaCl by RP-HPLC or gel electrophoresis.

TGF-$\beta$s exhibit activity in the TGF-$\beta$ assay described in *Methods for preparation of Media, Supplements, and substrate for serum-free Animal Cell Culture* (1984) pp 181–194, Alan R. Liss, Inc. That assay determines ability to induce anchorage-independent growth in non-neoplastic normal rat kidney fibroblasts by measuring the formation of cell colonies in soft agar. Procedures for obtaining TGF-$\beta$s from platelets, placenta, and kidney tissues are described in International patent publication WO 84/01106 and EPA publication number 0128849. Briefly, this involves extracting the source material with acid-ethanol, sizing the extract by gel filtration, and isolating the TGF-$\beta$ from the filtrate by high performance liquid chromatography (HPLC).

TGF-$\beta$s isolated to date are nonspecies specific as regards TGF-$\beta$ activity. It is believed, therefore, that these polypeptides have been highly conserved among animal species (i.e, a given polypeptide from different mammalian species has an amino acid sequence that varies, if at all, in one or more amino acid residue deletions, additives, or substitutions that do not affect the non-species specific activity of the molecule adversely) and have cross-species functionality. For example, murine TGF-$\beta$1 has been shown to differ from human TGF-$\beta$1 by only one amino acid (Derynck et al., *J. Biol. Chem.* 261:4377, 1986), while murine TGF-$\beta$2 differs from human TGF-$\beta$2 by only three amino acids (Miller et al., *Mol. Endo.* 3:1108, 1989). Bovine TGF-$\beta$1 and TGF-$\beta$2 have completely identical amino acid sequences to human TGF-$\beta$1 and TGF-$\beta$2, respectively (Ogawa and Seyedin, *Meth. Enz.* Vol 198, in press). Human TGF-$\beta$3 differs from chicken TGF-$\beta$3 by only one amino acid residue, but is identical to murine TGF-$\beta$3 (Denhez et al., *Growth Factors* 3:139, 1990). Accordingly, the TGF-$\beta$s may be derived from cells or tissue of diverse animal origin or may be obtained by recombinant DNA technology. Correlatively, TGF-$\beta$ from one vertebrate species may be used to treat another vertebrate species. The most common therapeutic usages of TGF-$\beta$ will be in the treatment of humans, domestic animals such as cattle, sheep, and pigs, and sports or pet animals such as dogs, cats, and horses.

The TGF-$\beta$2.3 of the invention may be useful by itself or in combination with cofactors for inducing cartilage/bone formation for repairing, replacing, or augmenting cartilage/bone tissue in animals including humans. Chondrogenically/osteogenically effective amounts of the proteins will normally be formulated with pharmacologically and physiologically acceptable fluid or solid carriers for implantation.

The TGF-$\beta$2.3 of the present invention may also be useful as a diagnostic reagent for detecting cancers, neoplasms, and other disorders involving the production of TGF-$\beta$2, TGF-$\beta$3, or TGF-$\beta$2.3. Purified TGF-$\beta$2.3 may be used as the reagent itself, or alternatively, monoclonal or polyclonal antibodies directed against TGF-$\beta$2.3 may be used as the diagnostic reagent in such diagnostic assays.

The TGF-$\beta$2.3 of the invention may also be used in the same manner as other TGF-$\beta$s to promote (provoke and sustain) non-species specific cellular proliferation. Clinical applications of the cell proliferation activity of these compositions include topical administration for burn or wound healing or tissue repair. In such uses the proteins and activating agent will be formulated in amounts sufficient to induce soft tissue cell proliferation with pharmaceutically acceptable carriers that are added for the particular mode of administration. Topical dosage forms will typically be formulated as sprays, gels, ointments, or salves. Implants will be formulated as injectables. Systemic dosage forms may be formulated for enteral administration (i.e., liquids, pills, tablets) or for parenteral injection. The dosages used in such applications cannot be specified because of the nature of all proliferation activity and the variability in wounds and other trauma.

The TGF-$\beta$2.3 may also be useful for treating bone deficiencies, such as osteoporosis and osteopetrosis, systemically. For such treatment the TGF-$\beta$2.3 will be formulated in therapeutically effective amounts with injectable carriers and administered parenterally to the patient. Doses will typically be in the range of 0.001 µg/kg to 10 mg/kg.

TGF-$\beta$s may be used as oncostats in treating any type of cellular neoplasm, including, without limitation, carcinomas, myelomas, melanomas, and lymphomas. Particularly preferred targets are breast, lung, colon, and ovarian carcinomas. The TGF-$\beta$s may be administered locally or systemically, depending on the nature and degree of the neoplasm being treated. For local administration an oncostatically effective amount of TGF-$\beta$2.3 or mixtures formulated thereof with a pharmaceutically acceptable carrier as an injectable for parenteral administration, or as a solid or semisolid implant which may or may not be of a sustained or a controlled release form.

Alternatively, the oncostats could be delivered to solid tumors in particular, including inoperable tumors using current catheter technology for localized delivery via the arterial supply to the tumor. In this situation the oncostat could be mixed with a vasoocclusive agent, such as injectable collagen, which would provide a means to reduce perfusion of the tumor and at the same time provide for the localized delivery of the oncostatic agent. Clips may also be used to occlude venous drainage, and thus maintain high doses of TGF-$\beta$2.3 in the tumor mass.

For systemic administration, oncostatically effective amounts of TGF-$\beta$2.3 will be formulated with conventional carriers used for water soluble proteins (e.g. physiological saline, sugar solutions and the like) for injection into circulation. Alternatively, they may be formulated as a sustained release formulation that releases the TGF-$\beta$2.3 to circulation over a prolonged time period. Specific targeting of the factor for tumor cells in systemic applications may be accomplished by conjugation of the TGF-$\beta$2.3 to an antibody directed against tumor specific cell surface antigen(s). Enhanced tumor cell cytotoxicity may be accomplished by covalently radiolabelling the TGF-β2.3 with $^{131}$I, a cytotoxic agent. The TGF-βs are readily iodinated and retain full biological activity. Monoclonal antibody preparations with specificity for particular tumor types, such as breast and ovarian tumors, are well known in the art. Other oncostats of chemotherapeutic drugs may be included in the formulation if desired.

The term "oncostatically effective" is intended to indicate a dose that effects a significant (>50%) inhibition of tumor cell proliferation. In in vitro assays, 50% inhibition is generally observed at TGF-β concentrations of the order of 0.2 µg/ml or lower and saturation is achieved at 10 µg/ml or lower. Inhibition may be monitored in vivo by monitoring the patient's tumor burden. The amount of TGF-β2.3 which is oncostatically effective in a given treatment will depend upon the patient, the type and degree of cancer being treated and the mode of administration. In general, the amounts administered to adult humans will be in the range of about 0.001 µ/kg to 10 mg/kg. Corresponding systemic administration will involve the higher segment of the range (0.01 µg/kg to 10 mg/kg) due to the clearance or other in situ inactivation of the polypeptide.

The TGF-β2.3 of the instant invention may be useful in the treatment of both local and systemic inflammation. When used as a local anti-inflammatory agent the TGF-β2.3 will usually be formulated in effective amounts with pharmaceutically acceptable carriers in weight ratios to carrier in the range of 1:1000 to 1:20000. If tissue deposition at the site is not desired, the level of TGF-β2.3 to carrier may be lowered to below that (e.g. at weight ratios below 1:6000 in the case of collagen carrier which promotes tissue deposition. In addition to being formulated as an injectable, the TGF-β2.3 may be incorporated (dispersed) into solid permeable implants such as collagenous soft and hard tissue implants, prostheses, sponges, wound dressings, and sutures to modulate local inflammatory responses to solid bodies. Since such implants are made from permeable materials the TGF-β2.3 can diffuse from the implant and exert its antiinflammatory properties.

When used to treat inflammation at internal sites locally, the TGF-β2.3 may be injected, inhaled, placed surgically, or otherwise administered locally, depending on the particular formulation, and the site where inflammation control is desired.

For systemic administration TGF-β2.3 may be formulated with conventional carriers used with water soluble proteins for injection into circulation. Alternatively, it may be formulated as a sustained release implant formulation if the indication being treated so requires.

The amount of TGF-β2.3 administered to treat inflammation will depend upon the patient, the inflammatory condition being treated, and the mode of administration. In general, amounts administered to adult humans will be in the range of about 0.001 µg/kg to 10 mg/kg. When the TGF-β2.3 is administered locally, amounts in the lower portion of the range will normally be used, typically 0.1 to 10 µg. Correspondingly, systemic administration will typically involve amounts in the 10–1000 µg range.

TGF-β2.3 may be particularly effective in the treatment of inflammation involving the respiratory system. In this application, the TGF-β2.3 may be administered by inhalation with a suitable aerosol. In this form, these factors would be useful for the treatment of diffuse interstitial diseases of the lung such as asbestosis, silicosis, or coal-minor's pneumoconiosis; the treatment of immunological diseases that involve the respiratory tract such as rheumatoid arthritis, lupus erythematosus, or Goodpasture's syndrome; and the treatment of granulomatosis and eosinophilic granulomatosis.

These anti-inflammatory peptides may be combined with carriers in the form of a salve, ointment, or other topical formulation and thereby be useful in the control of dermal inflammation by topical application. Such formulations would be particularly useful in the local treatment of psoriasis vulgaris, contact dermatitis, dermal ulcers, and acute or chronic eczematous dermatitis.

TGF-β2.3 may be either used alone or combined with a slow release carrier and injected into or around joints, bone, or muscle for control of inflammation associated with various diseases. Some examples include myositis (viral, bacterial, parasitic, fungal, or autoimmune processes); myasthenia gravis; osteomyelitis; osteoarthritis and rheumatoid arthritis.

Since TGF-β molecules have been shown to be stable at low pH and resistant to enzyme digestion, these factors may be delivered systemically by ingestion. These properties make these factors particularly useful for the treatment of gastric and duodenal ulcers, granulomatous gastritis, esophagitis (numerous causes); enteritis (numerous causes); and colitis (numerous causes).

TGF-βs have also been shown to be effective for the treatment of septic shock (International Publication Number WO 90/000903, filed 21 Jul., 1989). TGF-β2.3 may be administered prophylactically or therapeutically, i.e., before, simultaneous with, or after an infection has set in. TGF-β2.3 may be used to treat patients who are at-risk with respect to bacterial infection, or who suffer from septicemia. Patients who are at risk include those receiving immunosuppressive therapy and those suffering from severe thermal burns or other serious injury, cystic fibrosis, renal failure, or cancer, or who are undergoing extensive surgical procedures or organ transplantation.

TGF-β2.3 may be administered to a these patients by any suitable technique, including systemic or local, as discussed above. Similarly, TGF-β2.3 compositions and doses may be formulated as discussed for above applications, taking into consideration the requirements of the individual patient, the cause of the septic shock, the method of administration, and other factors known to practitioners. Doses will typically be in the range of 0.001 μg/kg to 10 mg/kg.

TGF-β2.3 may be used to treat a patient for an indication associated with a dysfunction or malfunction of hematopoiesis or lymphopoiesis. TGF-β2.3 may be administered to a these patients by any suitable technique, including systemic or local, as discussed above. Similarly, TGF-β2.3 compositions and doses may be formulated as discussed for above applications, taking into consideration the requirements of the individual patient, the method of administration, and other factors known to practitioners. Doses will typically be in the range of 0.001 μg/kg to 10 mg/kg.

TGF-β may also be used to protect hematopoietic stems cells from the myelotoxicity of chemotherapeutic drugs, such as cyclophosphamide and mephalan, or radiation therapy. In such applications a therapeutically effective amount of TGF-β2.3 will be administered prior, usually 3–72 hours, to the administration of the chemotherapeutic drug or radiation therapy. The mode of administration is preferably interfemoral arterial, intraperitoneal, or subcutaneous, and is preferably by injection. TGF-β2.3 compositions and doses may be formulated as discussed for above applications, taking into consideration the requirements of the individual patient, the nature of the drug or radiation therapy used, the method of administration of the composition, and other factors known to practitioners. Doses will typically be in the range of 0.001 µg/kg to 10 mg/kg.

TGF-β may also be used in the prevention of severe cardiac injury resulting from reperfusion of ischemic myocardium (Lefer et al., Science 249:61, 1990). TGF-β2.3 may be administered, preferably intravenously, prior to or after the onset of ischemia. TGF-β2.3 compositions and doses may be formulated as discussed for above applications, taking into consideration the requirements of the individual patient and other factors known to practitioners. Doses will typically be in the range of 0.001 µg/kg to 10 mg/kg.

Recombinant Expression of TGF-β2.3

The proteins of the invention may be expressed in vitro, or in vivo in either prokaryotic or eukaryotic systems. Prokaryotes are most frequently represented by various strains of E. coli. However, other microbial strains may also be used, such as bacilli (for example Bacillus subtilis), various species of Pseudomonas, and other bacterial strains. In such prokaryotic systems, plasmid vectors which contain replication sites and control sequences derived from a species compatible with the host are used. For example, E. coli is typically transformed using derivatives of pBR322, a plasmid derived from an E. coli species by Bolivar et al., Gene 2:95, 1977. Commonly used prokaryotic control sequences, which are defined herein to include promoters for transcription initiation, optionally with an operator, along with ribosome binding site sequences, include such commonly used promoters as the β-lactamase (penicillinase) and lactose (lac) promoter systems (Chang et al, Nature 198:1056, 1977) and the tryptophan (trp) promoter system (Goeddel et al., Nuc. Acids Res. 8:4057, 1980) and the lambda-derived $P_L$ promoter and N-gene ribosome binding site (Shimatake et al., Nature 292:128, 1981). However, any available promoter system compatible with prokaryotes can be used.

The expression systems useful in eukaryotic systems of the invention comprise promoters derived from appropriate eukaryotic genes. A class of promoters useful in yeast, for example, include promoters for synthesis of glycolytic enzymes, including those for 3-phosphoglycerate kinase (Hitzeman et al., J. Biol. Chem. 255:2073, 1980). Other promoters include those from the enolase gene (M. J. Holland et al., J. Biol. Chem. 256:1385, 1981) or the Leu2 gene obtained from YEp13 (J. Broach et al., Gene 8:121, 1978).

Suitable mammalian promoters include the early and late promoters from SV40 (Fiers et al., Nature 273:113, 1978) or other viral promoters such as those derived from polyoma, adenovirus II, bovine papilloma virus, or avian sarcoma viruses. Suitable viral and mammalian enhancers are cited above. In the event plant cells are used as an expression system, the nopaline synthesis promoter is appropriate (Depicker et al., J. Mol. Appl. Gen. 1:561, 1982). Expression in insect cell culture may conveniently be achieved using a baculovirus vector.

Construction of suitable vectors containing the desired coding and control sequences employs standard ligation and restriction techniques which are well understood in the art. Isolated plasmids, DNA sequences, or synthesized oligonucleotides are cleaved, tailored and religated in the form desired.

Site specific DNA cleavage is performed by treatment with a suitable restriction enzyme (or enzymes) under conditions which are generally understood in the art, generally following the manufacturer's directions. See, e.g., New England Biolabs, Product Catalog. In general, about 1 µg of plasmid or DNA sequence is cleaved by one unit of enzyme in about 20 µl of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein may be removed by extraction with phenol/chloroform, and may be followed by diethyl ether extraction, and the nucleic acid recovered from aqueous fractions by ethanol precipitation followed by separation over a Sephadex® G-50 spin column. If desired, size separation of the cleaved fragments may be performed by polyacrylamide gel or agarose gel electrophoresis using standard techniques. A general description of size separations is found in Meth. Enzymol. 65:499–560, 1980.

Single-strand "ends" of restriction cleaved fragments may be removed or converted to a double-strand form ("blunt-ended") by treating with the large fragment of E. coli DNA polymerase I (Klenow) in the presence of the four deoxyribonucleotide triphosphates (dNTPs) using incubation times of about 15 to 25 min at 20 to 25° C. in 50 mM Tris, pH 7.6, 50 mM NaCl, 6 mM $MgCl_2$, 6 mM DTT and 5–10 µM dNTPs. The Klenow fragment adds deoxyribonucleotides at 5' "sticky ends" but hydrolyzes protruding 3' single strands, even though the four dNTPs are present. If desired, selective repair can be performed by supplying only 1–3 of the dNTPs, within the limitations dictated by the nature of the sticky ends. After treatment with Klenow fragment, the mixture is extracted with phenol/chloroform and ethanol precipitated followed by chromatography on a Sephadex G-50 column. Treatment under appropriate conditions with S1 nuclease results in hydrolysis of any single-stranded portion.

Synthetic oligonucleotides are prepared by the triester method of Matteucci et al. (J. Am. Chem. Soc. 103:3185, 1981) or using commercially available automated oligonucleotide synthesizers. Labeling of single strands prior to annealing is achieved using an excess, e.g., approximately 10 units of polynucleotide kinase to 0.1 nmole substrate in the presence of 50 mM Tris, pH 7.6, 10 mM $MgCl_2$, 5 mM dithiothreitol, 1–2 mM ATP, 1.7 pmoles $^{32}$P-ATP (2.9 mCi/mmole), 0.1 mM spermidine, and 0.1 mM EDTA.

Ligations are performed in 15–30 µl volumes under the following standard conditions and temperatures: 20 mM Tris-HCl, pH 7.5, 10 mM $MgCl_2$, 10 mM DTT, 33 µg/ml BSA (bovine serum albumin), 10 mM–50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

Correct ligations for plasmid construction may be confirmed by first transforming E. coli strain MM294 obtained from E. coli Genetic Stock Center, CGSC #6135, or other suitable host with the ligation mixture. Successful transformants are selected by ampicillin, tetracycline or other antibiotic resistance or using other markers depending on the plasmid construction, as is understood in the art. Plasmids from the transformants are then prepared according to the method of D. B. Clewell et al, Proc. Natl. Acad. Sci. U.S.A. 62:1159, 1969, optionally following chloramphenicol amplification (D. B. Clewell, J. Bacteriol. 110:667, 1972). The isolated DNA is analyzed by restriction and/or sequenced by the dideoxy method of F. Sanger et al., Proc.

*Natl. Acad. Sci. U.S.A.* 74:5463, 1977, as further described by Messing et al., *Nucleic Acids Res.* 9:309, 1981, or by the method of Maxam et al., *Meth. Enzymol.* 65:499, 1980.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{2+}$ using about 1 unit of BAP per µg of vector at 60° C. for about 1 hr. In order to recover the nucleic acid fragments, the preparation is extracted with phenol/chloroform and ethanol precipitated and desalted by application to a Sephadex G-50 column. Alternatively, religation can be prevented in vectors which have been double-digested by additional restriction enzyme digestion of the unwanted fragments.

For portions of vectors derived from cDNA or genomic DNA which require sequence modifications, site-specific primer directed mutagenesis may be used. This is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having the mutated form as a single strand; 50% will have the original sequence. The resulting plaques are hybridized with kinased synthetic primer under allele-specific conditions. In general, one may vary the temperature, ionic strength, and concentration of chaotropic agent(s) in the hybridization solution to obtain conditions under which substantially no probes will hybridize in the absence of an "exact match." For hybridization of probes to bound DNA, the empirical formula for calculating optimum temperature under standard conditions (0.9M NaCl) is $$T(°C.)=4(N_G+N_C)+2(N_A+N_T)-5° C.,$$

where $N_G$, $N_C$, $N_A$, and $N_T$ are the numbers of G, C, A, and T bases in the probe (J. Meinkoth et al., *Anal. Biochem.* 138:267, 1984). Plaques which hybridize with the probe are then picked, cultured, and the DNA recovered.

When a vector is used that requires transformation of the host cell, transformation of the host cell with a recombinant construct is done using standard techniques appropriate to such cells. The calcium treatment employing calcium chloride, as described by Cohen, *Proc. Natl. Acad. Sci. U.S.A.* 69:2110, 1972, or the RbCl method described in Maniatis et al., *Molecular Cloning: A Laboratory Manual* (1982) Cold Spring Harbor Press, p. 254, is used for prokaryotes or other cells which contain substantial cell wall barriers. Infection with *Agrobacterium tumefaciens* (Shaw et al., *Gene* 23:315, 1983) is used for certain plant cells. For mammalian cells without cell walls, the calcium phosphate precipitation method of Graham and van der Eb, *Virology* 52:546, 1978 is preferred. Transformations into yeast are carried out according to the method of Van Solingen et al., *J. Bac.* 130:946, 1977, and C. L. Hsiao et al., *Proc. Natl. Acad. Sci. U.S.A.* 76:3829, 1979. Alternatively, one may use a liposomal transfection system. For example, one may use a synthetic lipid such as N-[1-(2,3-dioleyloxy)propyl]-N, N,N-trimethylammonium chloride, commercially available under the name Lipofectin (BRL, Gaithersburg, Md.), as described by P. L. Felgner et al., *Proc. Natl. Acad. Sci. U.S.A.* 84:7413, 1987.

The cDNA or genomic libraries resulting from any of the transformation methods described above are screened using the colony hybridization procedure. Each microtiter plate is replicated onto duplicate nitrocellulose filter papers (S & S type BA-85) and colonies are allowed to grow at 37° C. for 14–16 hr on L agar containing 50 µg/ml ampicillin. The colonies are lysed and DNA fixed to the filter by sequential treatment for 5 min with 500 mM NaOH, 1.5M NaCl, and are washed twice for 5 min each time with 5× standard saline citrate (SSC). Filters are air dried and baked at 80° C. for 2 hr. The duplicate filters are prehybridized at 42° C. for 6–8 hr with 10 ml per filter of DNA hybridization buffer (5× SSC, pH 7.0, 5× Denhardt's solution (polyvinylpyrrolidone, plus Ficoll and bovine serum albumin; 1×=0.02% of each), 50 mM sodium phosphate buffer at pH 7.0, 0.2% SDS, 20 µg/ml poly-U, and 50 µg/ml denatured salmon sperm DNA).

The samples are hybridized with kinased probe under conditions which depend on the stringency desired. Typical moderately stringent conditions employ a temperature of 42° C. for 24–36 hr with 1–5 ml/filter of DNA hybridization buffer containing probe. For higher stringencies, high temperatures and shorter times are employed. The filters are washed four times for 30 min each time at 37° C. with 2× SSC, 0.2% SDS and 50 mM sodium phosphate buffer at pH 7, then washed twice with 2× SSC and 0.2% SDS, air dried, and are autoradiographed at −70° C. for 2 to 3 days.

Probes for detection of the desired recombinant construct may be prepared as follows. Nucleic acid binding partners are prepared by means known to those of ordinary skill in the art, for example by cloning and restriction of appropriate sequences or preferably by direct chemical synthesis. For example, one may employ the phosphotriester method described by S. A. Narang et al., *Meth. Enzymol.*, 68:90, 1979, and U.S. Pat. No. 4,356,270, incorporated herein by reference. Alternatively, one may use the phosphodiester method disclosed in E. L. Brown et al, *Meth. Enzymol.* 68:109, 1979, incorporated herein by reference. Other methods include the diethylphosphoramidite method disclosed in Beaucage et al., *Tetrahedron Lett.*, 22:185, 1981, and the solid support method disclosed in U.S. Pat. No. 4,458,066. The binding partners may also be labeled, if desired, by incorporating means detectable by spectroscopic, photochemical, biochemical, immunochemical, or chemical means. For example, the primer may include $^{32}$P, fluorescent dyes, electron-dense reagents, enzymes (as commonly used in ELISAs), biotin, or haptens or proteins for which antisera or monoclonal antibodies are available.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50–200 µg/injection is typically sufficient. Immunization is generally boosted 2–6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization.

Polyclonal antisera is obtained by bleeding the immunized animal into a glass or plastic container, incubating the blood at 25° C. for one hour, followed by incubating at 4° C. for 2–18 hours. The serum is recovered by centrifugation (e.g., 1,000 ×G for 10 minutes). About 20–50 ml per bleed may be obtained from rabbits.

Monoclonal antibodies are prepared using the method of Kohler and Milstein, *Nature* 256:495, 1975, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B cells expressing membrane-bound immunoglobulin specific for the antigen bind to the plate, and are not rinsed away with the rest of the suspension. Resulting B cells, or all dissociated spleen cells, are then induced to fuse with myeloma cells to form hybridomas, and are cultured in a selective medium (e.g., hypoxanthine, aminopterin, thymidine medium, "HAT") The resulting hybridomas are plated by limiting dilution, and are assayed for the production of antibodies which bind specifically to the immunizing antigen (and which do not bind to unrelated antigens). The selected monoclonal antibody (MAb)-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, I may serve as a radioactive label or as an electron-dense reagent. Horseradish peroxidase (HRP) may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

Antibodies reactive with TGF-β neutralize the biological activity of TGF-β by preventing the antigen from binding to its cell surface receptors. The intact antibody, antigen binding fragments (e g., Fab', F(ab')$_2$) may be useful in these applications. In addition, administration of anti-TGF-β2.3 antibodies would form immune complexes (antigen-antibody) complexes that will increase the rate at which the antigen TGF-β is cleared from the systemic circulation or from the tissue site where the antigen is produced.

Fibrotic diseases and tumor cells may be treated by administering a therapeutically effective amount of anti-TGF-β2.3 antibodies to affect the inhibition of fibrosis formation or regression of tumor cells. The method and frequency of administration, the dose range, and the duration of antibody therapy will vary with the severity and nature of the condition, and the general health of the patient.

In a preferred embodiment, the antibodies of the present invention are administered locally to the affected tissue sites by bolus injection or perfusion. The amount of antibody administered may be measured by maintaining the local tissue concentration of TGF-β at about 1–1000 μg/ml.

Indications where this mode of treatment is particularly useful are for the control of excessive scar tissue formation, due to surgery or trauma, or prevention of the formation of connective tissue adhesions. For the treatment of tumor cells by local administration, the antibodies may be delivered directly into a solid tumor mass through a vascular catheter for deep solid tumors, or through a hypodermic needle for superficial or cutaneous tumors. The antibodies may be locally administered by a single bolus injection that is repeated over several days, or by continuous administration by perfusion. The amount of antibody administered is preferably about 1 μg up to 1000 μg/g tumor tissue.

In another embodiment, the antibodies may be administered systemically by intravenous or peritoneal perfusion, or by bolus injection into the subcutaneous tissue or muscle. The antibody may be delivered in vehicles generally known to those skilled in the art, such as saline, balances salt solution, isotonic or phosphate buffered saline (pH 7), with or without dextrose.

Indications where this mode of treatment is particularly useful are systemic diseases such as interstitial lung fibrosis, liver cirrhosis, scleroderma, and metastatic cancer.

For both local and systemic administration, antibodies reactive with TGF-β2.3 may be administered in combination with other antibodies reactive with TGF-β to reduce the amount of bioavailable factor.

Experimental

The following examples are intended to illustrate specific embodiments of the invention. They are not intended to limit the invention in any matter.

A. Isolation of TGF-β2.3

Bovine bone was processed as described in, for example, U.S. Pat. No. 4,843,063, to purify TGF-β2. After cation exchange chromatography, fractions containing the peak of TGF-β2 were identified and pooled.

Figure 2:
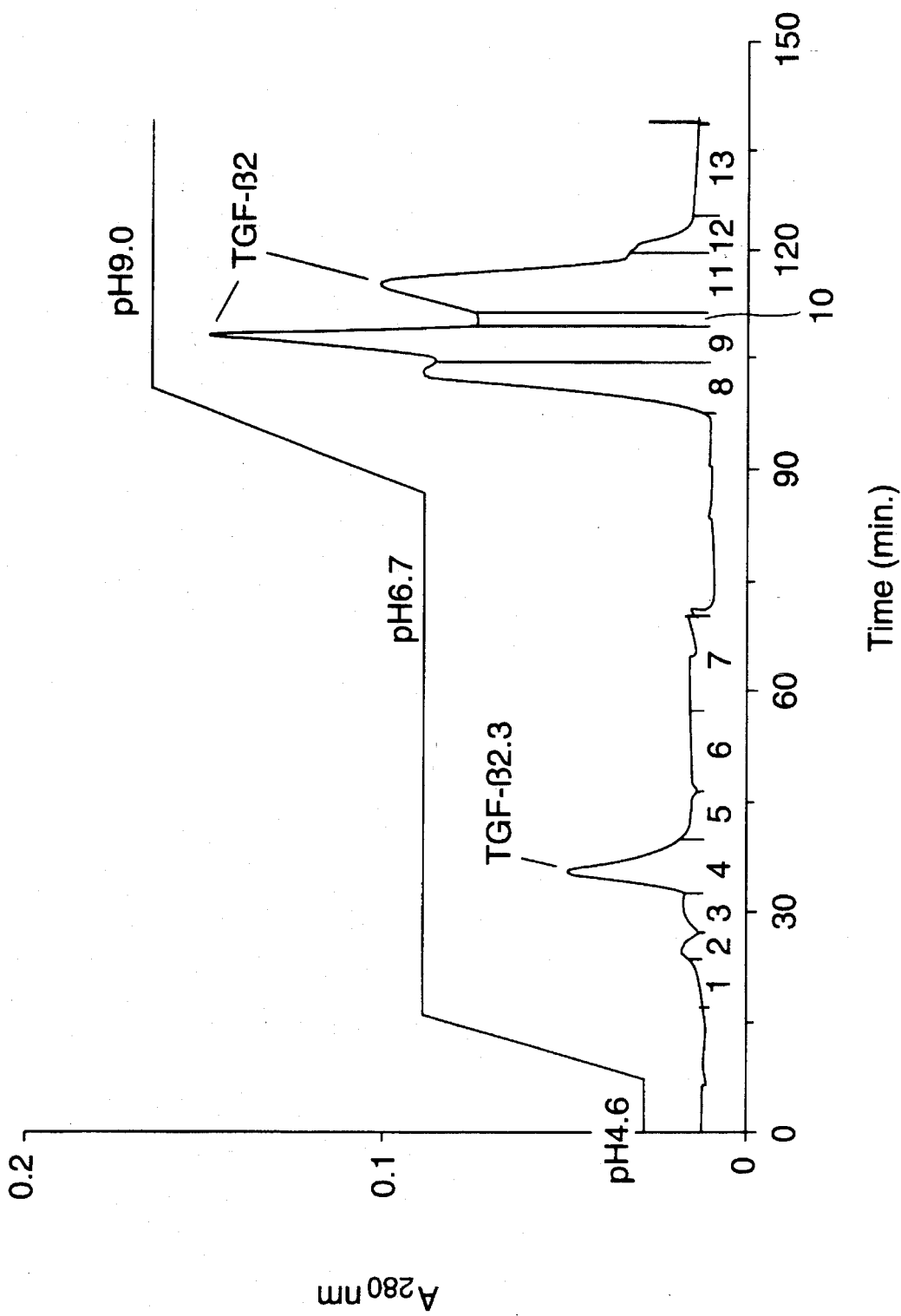
FIG. 2 is the elution profile on a Mono-S FPLC column in a pH 4.6 to 6.7 and pH 6.7 to 9.0 gradient of a TGF-β2 peak fraction, prepared as in FIG. 1, the pH 4.6 to 6.7 gradient fraction having a slightly slower mobility in SDS-PAGE than other TGF-β2 peak fractions.

This pool was applied onto a C18 reverse-phase HPLC column (1×25 cm, 5 μ, Vydac, 218TP510) and the bound proteins were eluted with a linear acetonitrile gradient in 0.1% TFA (FIG. 1). SDS-PAGE of the fractions revealed that the majority of the fractions contained a major band migrating at 25 KD. However, in a fraction (fraction #5) which eluted between the peaks of TGF-β1 and TGF-β2, the band migrated slightly slower than in the other fractions. Fraction #5 was applied onto a Mono-S FLPC column (0.5×5 cm, Pharmacia, HR5/5), which had been equilibrated into 6M urea, 50 mM sodium acetate, 10 mM NaCl, 1% isopropanol, pH 4.6. The column was equilibrated into 6M urea, 50 mM sodium acetate, 10 mM NaCl, 1% isopropanol, pH 6.7, over a 10 minute period at a flow rate of 0.5 ml/min to raise the pH to 6.7. The column was then equilibrated into 6M urea, 20 mM HEPES, 10 mM NaCl, 1% isopropanol, pH 6.7. Finally, the column was equilibrated into the buffer of the same composition, but at pH 9.0, over 10 minutes at flow rate of 0.5 ml/min. Some protein eluted during the pH 4.6 to 6.7 gradient, but the majority of the TGF-β2 eluted during the pH 6.7 to 9.0 gradient (FIG. 2).

Figure 3:
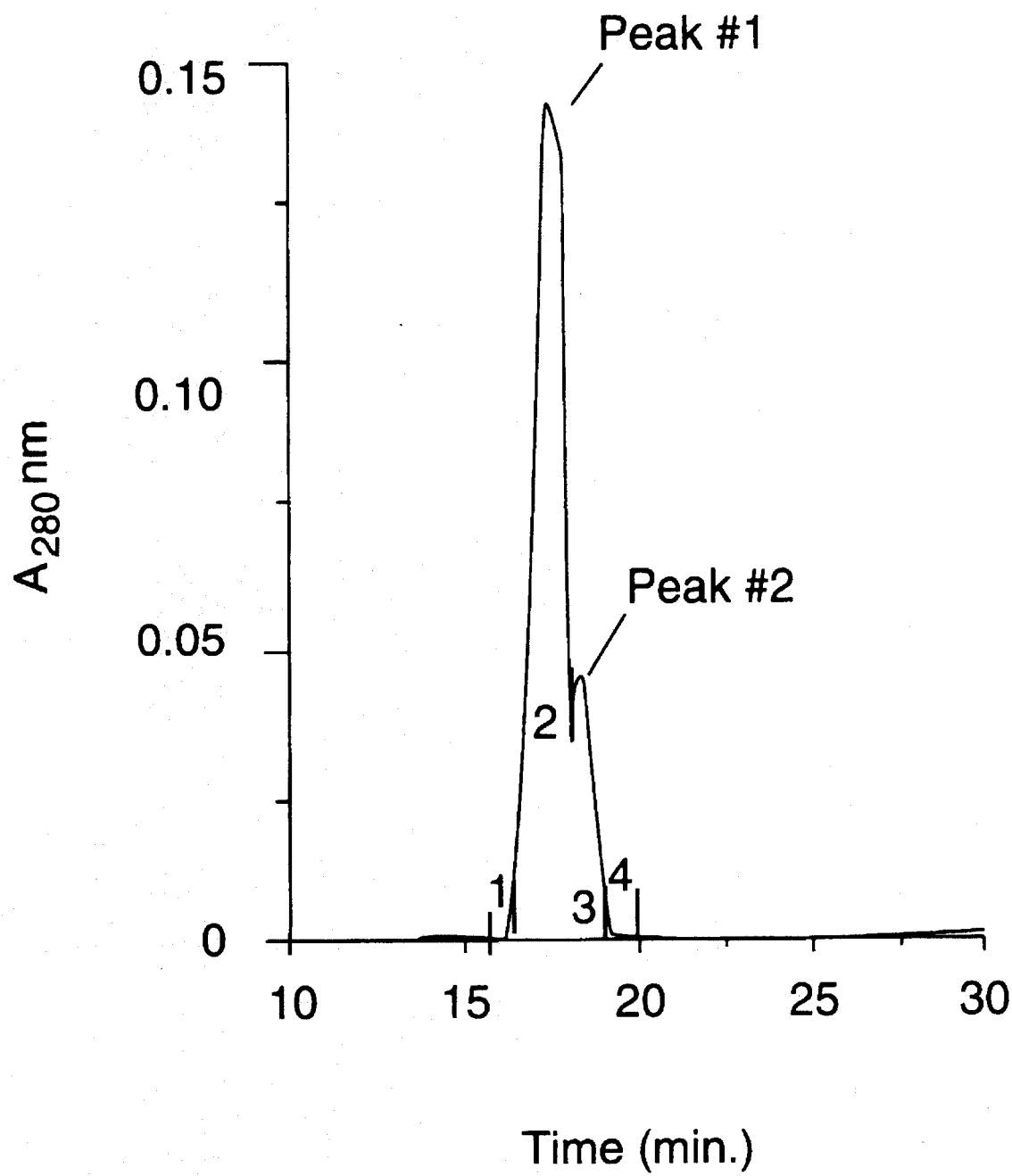
FIG. 3 is the elution profile of a fraction containing predominately 25 KD protein obtained from a pH 4.6 to pH 6.7 shift on a Mono-S FPLC column, chromatographed on a C18 reverse phase HPLC column in a linear acetonitrile gradient. The protein eluted as one major peak with a minor peak overlapping on the backside.

SDS-PAGE analysis of the pH 4.6–6.7 fractions revealed that fraction #4 consisted of predominately 25 KD protein. This #4 fraction containing the 25 KD protein in the pH 4.6–6.7 gradient was chromatographed on a C18 reverse-phase HPLC column (0.46×25 cm, Vydac, 5μ, 218TP54). The protein was eluted with a linear acetonitrile gradient in 0.1% TFA. The protein eluted as one major peak (peak #1) with a minor peak (peak #2) overlapping on the back side of the major peak (FIG. 3). SDS-PAGE showed that both major and minor peaks contained one single band at 25 KD under non-reducing conditions and 12 KD to 13 KD under reducing conditions, which are consistent with TGF-β.

Figure 4:
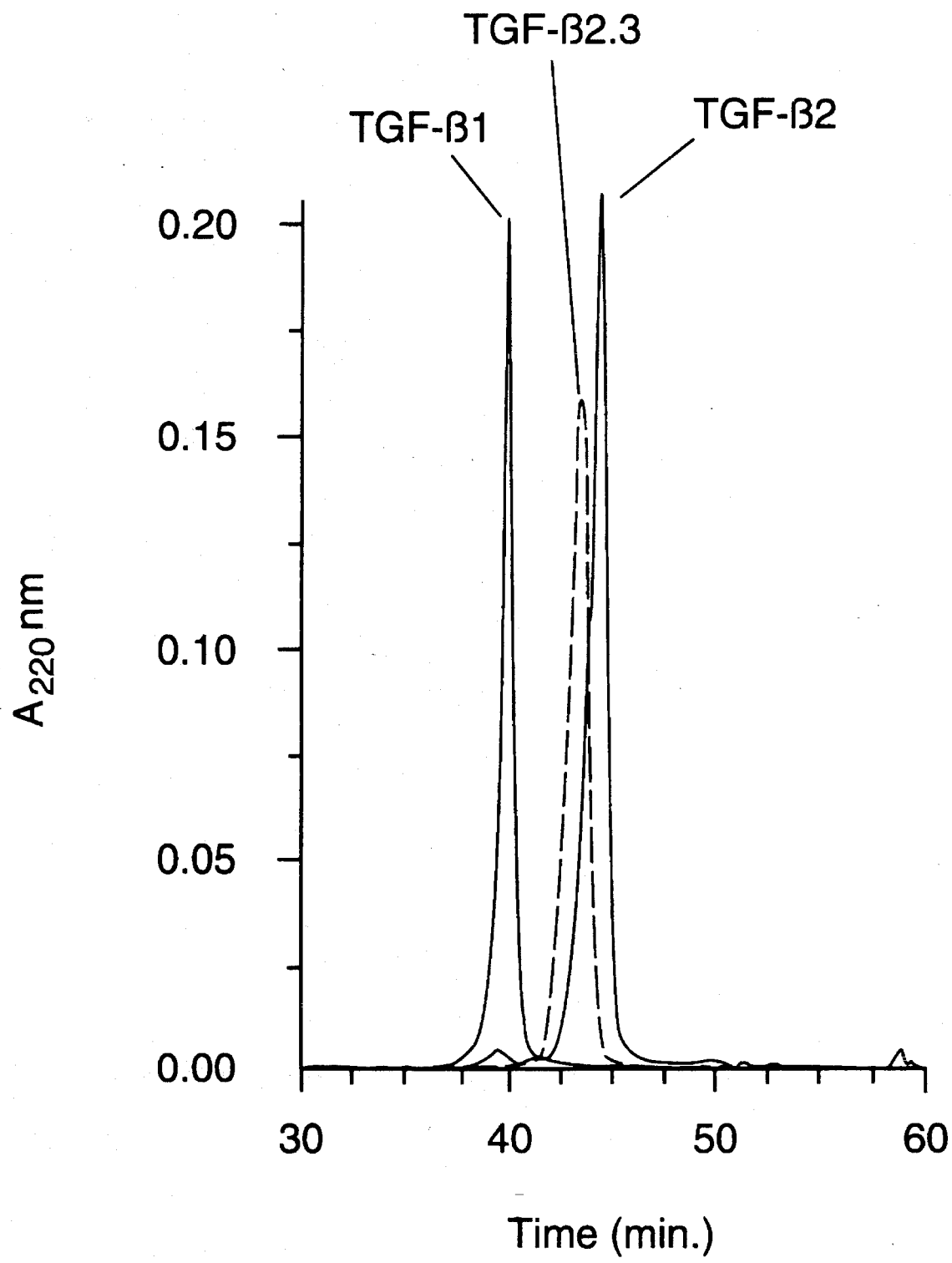
FIG. 4 is a comparison of the elution profiles of TGF-β2.3 with TGF-β1 (SEQ ID NO:1) and TGF-β2 from a C18 reverse phase HPLC column in an acetonitrile gradient in 0.1% TFA.
Figure 5:
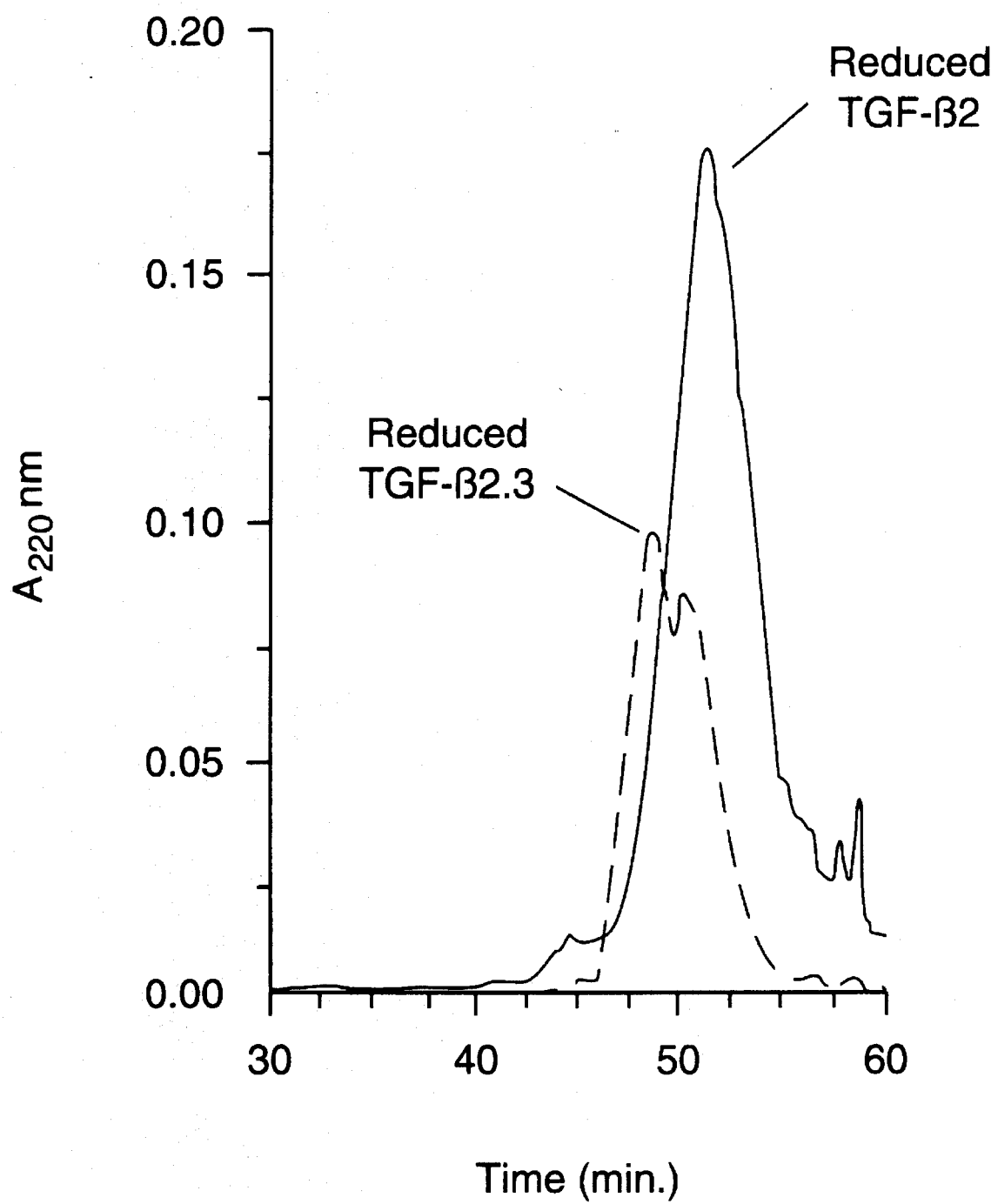
FIG. 5 is the elution profile of reduced TGF-β2.3 as two peaks from a C18 reverse phase HPLC column in an acetonitrile gradient in 0.1% TFA, the later eluting peak overlapping with the peak of reduced TGF-β2.

TGF-β1 eluted before TGF-β2 from the C18-reverse phase HPLC columns during acetonitrile gradient in 0.1% TFA. Under identical conditions, recombinant TGF-β3 has been reported to elute after TGF-β2 (Graycar et al., Mol Endo. 3: 1977–1986, 1989). The TGF-β2.3 heterodimer (peak #1) eluted as a single sharp peak slightly before TGF-β2, but after TGF-β1, under identical conditions (FIG. 4). When the protein was reduced with β-mercaptoethanol prior to HPLC, the protein then eluted in two peaks (FIG. 5). The position of the later eluting peak coincided with the position of the TGF-β2 peak when reduced. Results from immunoblots demonstrated that the later eluting peak contained predominately TGF-β2, while the earlier eluting peak contained predominately TGF-β3. The results were consistent with the identity of the 25 KD peak as a TGF-β2.3 dimer.

B. Cell Culture Assay

Mink lung epithelial cells (Mv1Lu, ATCC CCL 64) were cultured on 96 well tissue culture plates at a concentration of $1\times10^3$ cells per 50 μl MEM containing 10% fetal calf serum, penicillin, streptomycin, nonessential amino acids, and L-glutamine. Test samples were diluted in the culture medium and appropriate dilutions made. Samples of the diluted cells (50 μl) were added to the test wells in triplicate 30 minutes after plating. After incubation at 37° C. in a humidified 5% $CO_2$-95% air atmosphere for 4 days, the wells were rinsed with PBS (phosphate buffered saline) and filled with 100 μl of 0.1M sodium acetate, pH 5.5, 0.1% Triton X-100, 10 mM p-nitrophenol phosphate to lyse the cells. The growth of the cells was measured by assaying a constitutively expressed enzyme, acid phosphatase. After 2 hr, 10 μl of 0.1N NaOH was added to each well. Absorbance was measured on a multichannel plate reader at an absorbance setting of 405 nm and a reference filter setting of 492 nm. Inhibition-stimulation of growth was expressed in per cent decrease of the acid phosphatase activity in the treated cells when compared to the activity in untreated cells.

The protein from peaks #1 and #2 from the reverse-phase HPLC inhibited proliferation of mink lung epithelial cells (Mv1Lu, ATCC CCL64) with an $ED_{50}$ of 0.02 ng/ml and 0.025 ng/ml, respectively. TGF-β1 and TGF-β2 have an $ED_{50}$ of 0.01–0.02 ng/ml. The result demonstrates that the TGF-β2.3 of the present invention has specific biological activity comparable to TGF-β1 and TGF-β2.

C. Amino terminus sequencing

The amino terminus of the protein of peak #1 was sequenced to residue 59. The sequence consisted of an equal mixture of TGF-β2 and TGF-β3 amino terminal residues (Table I). The TGF-β1 sequence was absent. Given a mixture of TGF-β2 with either TGF-β1 or TGF-β3, distinction between TGF-β1 and TGF-β3 can be made at residues # 9, 10, 11, 13, 19, 26, 33, 40, 45, 51, 52, 54, 57, and 58 within the first 59 residues. At residues # 11, 12, 13, 17, 33, 40, and 50, the signals of the residues that match TGF-β3 were present at approximately 50% level of the total peak signal (the other 50% is from TGF-β2). Beyond residue #40, signals became lost in the background and could not be identified definitively. Based on these comparisons of partial sequences of N-termini, molecular weight analyses, and biological activity, TGF-β2.3 appeared to consist of a polypeptide having substantial homology at the N-terminal amino acid sequence to TGF-β2 and a polypeptide having substantial homology at the N-terminal amino acid sequence to TGF-β3, both polypeptides being present in equal proportion.

D. Immunological characterization

The TGF-β2.3 protein of the present invention cross-reacted strongly with anti-TGF-β3 polyclonal antibody on immunoblots. The antibody does not recognize TGF-β2. The TGF-β2.3 of the present invention also cross-reacted strongly with 3C7.14.6 anti-TGF-β2 monoclonal antibody on immunoblots. The monoclonal antibody does not recognize TGF-β1. These results demonstrated that the TGF-β2.3 contained TGF-β2 and TGF-β3 epitopes.

Furthermore, the TGF-β2.3 cross-reacted as well as TGF-β2 with the 2G1 anti-TGF-β2 monoclonal antibody in an enzyme-linked immunosorbent assay (ELISA). The monoclonal antibody did not cross-react with TGF-β1 or TGF-β3, while the antibody cross-reacted only partially with a mixture of TGF-β2 and TGF-β3 homodimers. These results demonstrate that the TGF-β2.3 of the present invention is a heterodimer and not a mixture of TGF-β2 and TGF-β3 homodimers.

E. Expression of recombinant constructs to yield the heterodimer

The mature biologically active TGF-β2.3 heterodimer may be produced by cloning and expressing the full-length nucleotide sequence encoding the TGF-β2 and the TGF-β3 precursors or their functional equivalent in a host cell which processes the precursor correctly, so that a mature TGF-β2.3 heterodimer is produced having a biological activity that is virtually indistinguishable from that of the naturally occurring TGF-β2.3 heterodimer. Functional equivalents of the full length nucleotide sequence encoding the TGF-β2 and the TGF-β3 precursors include any DNA sequence which, when expressed inside an appropriate host cell, is capable of directing the synthesis, processing, and export of mature TGF-β2.3 heterodimer.

Hybrid precursor sequences encoding, for example, the TGF-β2 precursor sequence joined in-frame to the TGF-β3 mature sequence in place of the TGF-β2 mature sequence may be constructed and cloned into an appropriate host cell. A TGF-β2 precursor sequence with the TGF-β2 mature sequence is also cloned into the very same host cell to express both the hybrid and the TGF-β precursor sequences in that host cell. Simultaneous expression of the two constructs, consisting of one TGF-β2 precursor gene and one hybrid gene consisting of the TGF-β2 N-terminal signal peptide sequence and pro-region joined to TGF-β3 mature sequence, results in association of the two gene products and expression and production of the TGF-β2.3 heterodimer.

Similarly, a TGF-β3 precursor sequence joined in-frame to the mature TGF-β2 mature sequence in place of the TGF-β3 mature sequence, may be constructed and cloned into an appropriate host cell. More generally, cloning and expression of any two hybrid precursor sequences, consisting of mature TGF-β2 and TGF-β3 sequences joined to separate, but identical signal peptide and TGF-β pro-region sequences in the same host cell, result in production of the TGF-β2.3 heterodimer.

In a further method for production of recombinant TGF-β2.3, TGF-β2 and TGF-β3 monomeric peptide chains may be renatured separately to produce folded TGF-β monomers. Subsequently, these TGF-β2 and TGF-β3 monomers are bonded together through one or more cysteine disulfide bond pairs to form the TGF-β2.3 heterodimer. For this purpose, the TGF-β gene encoding the mature TGF-β sequence is cloned into a bacterial expression system, such as *E. coli*. TGF-β2 and TGF-β3 polypeptide chains are expressed separately in different expression systems. TGF-β2 and TGF-β3 polypeptide chains are purified and renatured to fold the peptide chain and to form intrachain disulfide bonds. TGF-β2 and TGF-β3 monomers are then joined together through an interchain disulfide bond to form the TGF-β2.3 heterodimer.

Thus, a new form of a TGF-β-type factor, its uses, and methods for its production, have been disclosed. Although the preferred embodiments of the subject invention have been described in some detail, it is understood that obvious variations can be made without departing from the spirit and the scope of the invention as defined by the appended claims.

What is claimed is:

1. Substantially pure TGF-β2.3 whose partial sequence is SEQ. ID NO:4; said TGF-β2.3 isolated by:
   (a) subjecting a pool of TGF-β peak fractions to reverse phase HPLC; and then
   (b) recovering the fraction containing said TGF-β2.3, said fraction migrating between TGF-β1 and TGF-β2.

2. A therapeutic composition for inducing cartilage/bone formation and for promoting cellular proliferation, said composition comprising:

(a) a therapeutically effective amount of TGF-β2.3 whose partial sequence is SEQ. ID NO:4, said TGF-β2.3 isolated by subjecting a pool of TGF-β peak fractions to reverse phase HPLC and then recovering the fraction containing TGF-β2.3, said fraction migrating between TGF-β1 and TGF-β2; and
   (b) a pharmaceutically acceptable carrier.

* * * * *